United States Patent
Schwoebel

(10) Patent No.: US 8,956,576 B2
(45) Date of Patent: Feb. 17, 2015

(54) ANALYTICAL SYSTEM AND METHOD OF USE

(75) Inventor: Wolfgang Schwoebel, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1536 days.

(21) Appl. No.: 12/193,846

(22) Filed: Aug. 19, 2008

(65) Prior Publication Data

US 2009/0049892 A1    Feb. 26, 2009

(30) Foreign Application Priority Data

Aug. 24, 2007  (EP) ................................ 07114985

(51) Int. Cl.
- *G01N 31/22* (2006.01)
- *G01N 33/487* (2006.01)
- *G01N 35/00* (2006.01)

(52) U.S. Cl.
CPC .... *G01N 33/48771* (2013.01); *G01N 33/48757* (2013.01); *G01N 2035/00683* (2013.01)
USPC ............................. 422/404; 422/68.1; 702/82

(58) Field of Classification Search
CPC .............. G01N 2035/00683; G01N 33/48771; A61B 2560/028
USPC ..................................... 422/404, 68.1; 702/82
See application file for complete search history.

(56) References Cited

U.S. PATENT DOCUMENTS

| | | | |
|---|---|---|---|
| 5,415,840 A * | 5/1995 | Sano et al. ........................ | 422/67 |
| 7,477,404 B2 * | 1/2009 | Schulat et al. ................. | 356/614 |
| 2007/0077175 A1 | 4/2007 | Harttig | |

* cited by examiner

*Primary Examiner* — Jonathan Hurst
(74) *Attorney, Agent, or Firm* — Krieg DeVault LLP

(57) ABSTRACT

A system and method of use is provided, relating to an analytical system in which a disposable unit configured to contain a plurality of test strips is inserted into a hand-held device, the test strips being successively presented at a measuring position by a drive provided with the device, wherein after a disposable unit is removed and replaced, the drive is activated to position the test strip that is first in order at the measuring position and it is determined whether the test strip is present, and if the first test strip is not present, the test strip that was presented last when the device was actuated is again positioned at the measuring position.

12 Claims, 2 Drawing Sheets ard>

ANALYTICAL SYSTEM AND METHOD OF USE

CLAIM OF PRIORITY

The present application is based on and claims priority to European Patent Application 07114985.0, filed Aug. 24, 2007, which is hereby incorporated by reference in its entirety.

TECHNICAL FIELD OF THE INVENTION

The present application relates to an analytical system and a working process, such as for blood sugar tests, in which a plurality of test elements is inserted in a given order into a device as a disposable unit, and the test elements are successively presented at a measuring position by a drive that can be coupled with the disposable unit.

BACKGROUND

A basic example of an analytical system is a system typically used by diabetics for blood sugar self-monitoring by carrier-bound rapid tests that have to be carried out several times daily. In this context, compact hand-held devices are used for this which, due to a substantially automated measuring process, ensure that the necessary steps can be simply and rapidly carried out even by laymen. Such an analytical device is available on the market under the trade name ACCU-CHEK® Compact. The known device operates with a drum magazine which can be replaced as a disposable and in which strip-shaped analytical test elements can be presented successively for a measurement by rotating the drum, which is divided into segments. However, when the drum is replaced, it is not identified as a new or already partially used magazine. Accordingly starting from the initial position, a movement is made to each drum segment until a usable unit or an existing test strip is found. Hence, in the extreme case a user must wait until all positions have been passed through and the last available test is reached. This also takes place when the drum compartment is only opened for an instrument demonstration or inspection purposes and is closed without changing the drum.

On this basis, one object of the present invention is to further improve the known systems in the prior art and to further increase user friendliness and process reliability by the simplest possible means.

SUMMARY

The combination of features stated in the independent claims is proposed to achieve the above stated object of the present invention as well as other objects that will be appreciated by those of ordinary skill in the art.

The present invention is based on the idea of controlling the positioning process on the basis of an examination of the first test position. Accordingly it is proposed according to the invention that after a predetermined device actuation, the drive is activated to position the test element that is in the predetermined first in order position at the measuring position and it is determined whether the test element can be used and if it is not possible to use the first test element, the unused test element that was presented last at the time of the predetermined device actuation is again positioned at the measuring position. If the first in order magazine position has a usable test element, then the system assumes that a new magazine has been inserted. If a usable element is missing at the first in order magazine position, then it moves to the magazine position which was last used before a device actuation which is associated with a possible magazine replacement. This process can be carried out largely without complicated aids and typically without a special magazine coding. This allows a test to be performed for the user without a major loss of time even when the last used magazine is inserted again. Moreover, because the device drive is not caused to check each and every test element position to find a usable test element, the energy supply of the system can be conserved, which is especially important for battery operated hand-held devices.

An identifier of the last presented test element is advantageously stored in the memory of the device such that the last presented test element can be brought into position again according to the identifier. This can for example be achieved by using position numbers for a stepwise positioning.

It is also possible that after the device has been actuated, the required travel path to position the first test element is registered and if the first test element cannot be used, the test element presented last is positioned again according to the previously registered travel path. The travel path can thus be determined according to the difference in the path between the test element located at the measuring position when the device is actuated and the first test element.

If the first test element is usable the process control assumes, without an additional check, that a new disposable magazine has been inserted in exchange so that in this case the test elements can be used for subsequent tests in the given order.

In one embodiment, when the test element presented last upon device actuation is unusable, a sequence of steps determined by the order of the test elements in the disposable unit is executed until a test element is usable. This also covers the case that the user arbitrarily inserts one of several partially used magazines.

In another embodiment, user friendliness is improved due to the fact that when a test element is usable, the test readiness of the device is indicated to the user.

In yet other embodiments, the system identifies one or more operations by the user as a device actuation, including, for example, the insertion of a disposable magazine, the locking of a device component, the closing of a device cover, and other operations that may be associated with a possible replacement of the disposable unit.

One embodiment provides that the test elements are arranged as test strips each in one allocated cavity and that the usability is determined by checking the presence of a test element in the respective cavity. In this connection it is also advantageous when the disposable unit is formed by a rotatable magazine and in particular a drum or disk magazine and when the order of test units is determined by the angular position of segments of the magazine. Thus, it is also possible to use a stack magazine in which the order is defined by the stack position.

In order to utilize batch-specific information, in one embodiment the disposable unit is provided with a code that can be scanned by the device, and the code is read between the device actuation and the positioning of the first test element. In this connection, the system uses a barcode as the code and scans the barcode without contact while the disposable unit is moved within the device, such as by rotation.

In yet other embodiments, the test elements used for measurements are counted by a counter of the device and stored in the counter until the disposable unit is replaced thus enabling a simplified positioning and disposable identifier.

The present invention also relates to embodiments of an analytical system for patient self-monitoring, such as for blood sugar tests, comprising a measuring device and a disposable unit that can be inserted therein which contains a plurality of test elements in a given order in which the test elements can be successively presented to a measuring position by a drive of the device which can be coupled with the disposable unit. In order to achieve the object described above it is proposed that after a predetermined device actuation, a detection unit determines the usability of the test element that is in a predetermined first in order position and that the drive is designed such that if the first test element is unusable, the test element that was presented last when the device was actuated is positioned at the measuring position.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figure 1:
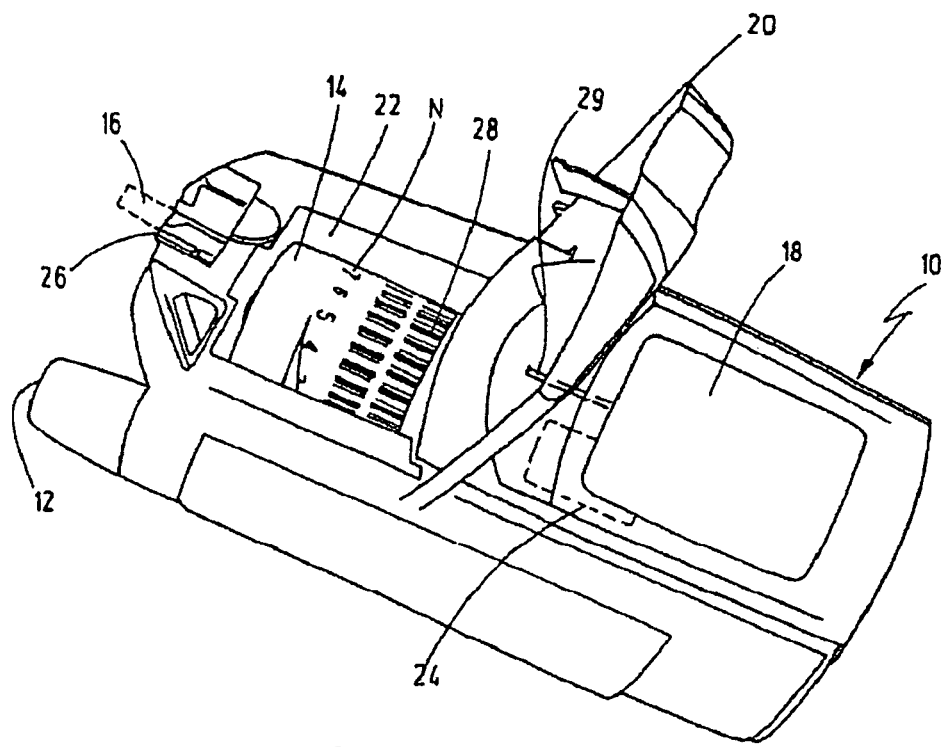
FIG. 1 illustrates an embodiment of an analytical system for analyte measurement in the form of a hand-held device containing a drum magazine for test strips.

The blood sugar measuring device 10 shown in FIG. 1 enables patient self-monitoring of the glucose content on the basis of a blood sample collected by means of the lancing aid 12 using a test strip drum 14 designed as a disposable unit which contains a plurality of analytical test strips 16. A test strip 16 loaded in each case with a drop of blood can be processed in a measuring device in the instrument that is not shown and the result of the measurement can be displayed locally to the user on a display 18.

As shown in FIG. 1 the test strip drum 14 is accessible in the drum compartment 22 when the device cover 20 is open so that it can, if necessary, be inspected by the user or removed for cleaning or replaced. After the cover 20 is closed, the test strip drum 14 is rotated by a rotary drive 24 into such a position that a test strip 16 can be presented at a measuring position 26 of the device 10. At the same time a barcode 28 affixed to the drum is read which informs the measuring device about the properties of the test strip 16.

After activating a button, the test strip 16 positioned in relation to the measuring position 26 is pushed out. This is carried out by a push rod 29 which engages in the drum 14 parallel to the axis of rotation. After the measurement the used test strip is ejected and the measuring device 10 counts the used strips 16 in a counter and indicates the number that are still available. Further details of the device are provided by DE-A 103 60 786 to which reference is herewith explicitly made and the disclosure of which is hereby incorporated herein by reference in its entirety.

Figure 2:
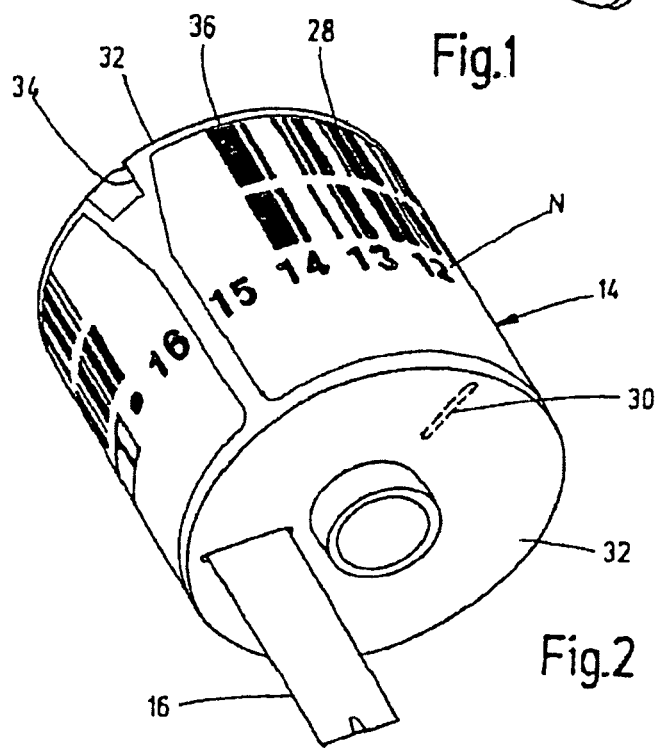
FIG. 2 illustrates an embodiment of a drum magazine that can be replaced as a disposable unit with a pushed-out test strip in a perspective view.

The test strip drum 14 shown in FIG. 2 has axially continuous strip chambers 30 that are arranged in a distributed fashion in the circumferential direction and in each of which a test strip 16 is arranged according to the position identifiers N. The front face of the drum 14 is closed by sealing foils 32 which can be pierced by the push rod 29 or the test strip 16 when it is pushed out. An index notch 34 can be provided for a defined drum positioning. Likewise the first code bar 36 of the barcode 28 can also be at a predetermined angular distance from the position N1 of the first test strip 16.

As already mentioned after a drum replacement or after closing the device cover 20, it should be ensured that a test strip 16 that can be pushed out linearly at the measuring position 26 is available. The corresponding positioning process provides that firstly the cavity 30 of the first test strip 16 (position N1) is positioned between the push rod 29 and measuring position 26 by rotating the drum. Consequently the device 10 firstly assumes in each case that an unused test strip drum 14 was inserted. Then the presence of the first test strip 16 is checked. If the first test strip is not present, the test strip (position Nx) that was presented last before the drum replacement is again presented by a suitable drum rotation. Hence, in this case it is assumed that the last used test strip drum 14 that was only partially used has been again inserted.

Figure 3:
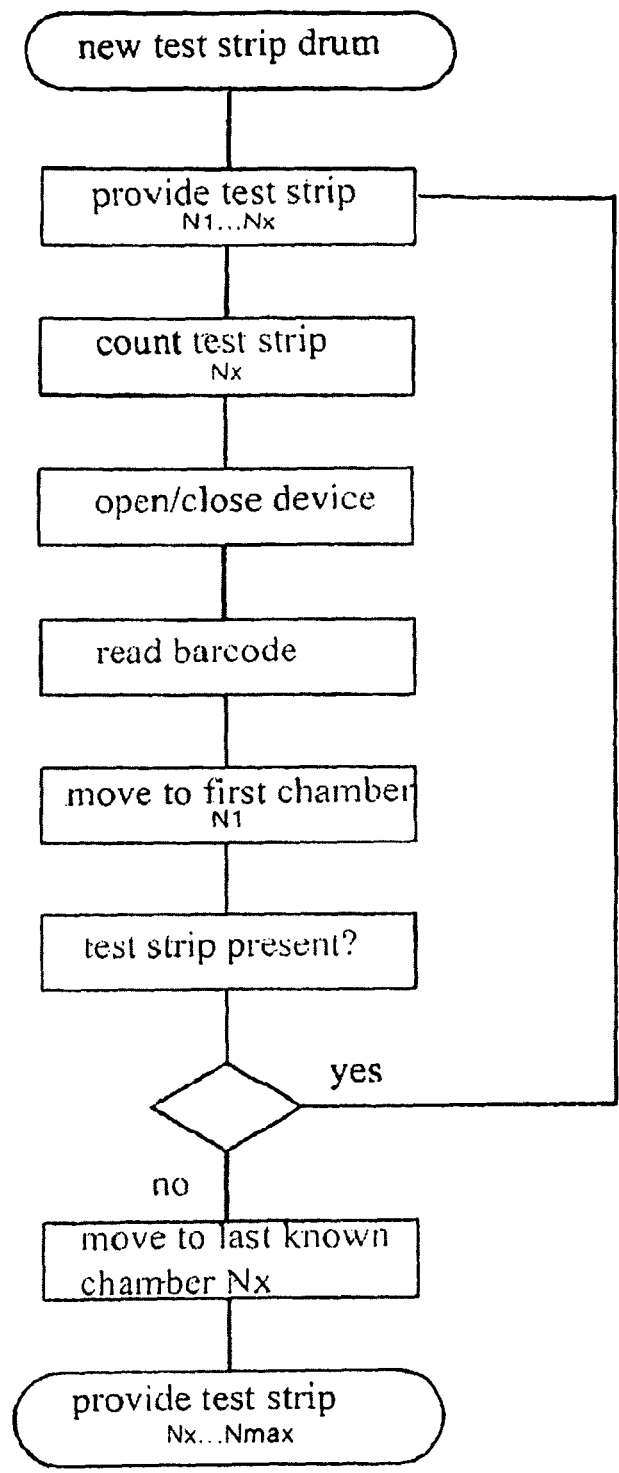
FIG. 3 illustrates a flow diagram of a positioning process when a drum magazine according to embodiments of the present invention is inserted.

The details of the process control are shown by the flow diagram of FIG. 3. After a new test strip drum has been inserted, the device 10 successively provides the test strips 16 for ejection at the measuring positions 26 by rotating the drum by the drive 24. The position number Nx of the strip that was presented last is stored in a counter.

After opening and closing the cover 20 the barcode is firstly read which requires a drum rotation relative to a permanent code reader in the device. In this process a batch code contained in the barcode can be detected and taken into account for the evaluation of the test.

In a next step the first cavity or chamber 30 is moved to the drum position N1, for example, which is positioned at the measuring position 26 opposite to the push rod 29. This can be carried out by a predetermined rotation distance starting at the index notch 34 or the first code bar 36. The presence of a test strip can be checked by a probing advance of the push rod 29 during which the required drive force is detected. When the sealing foil 32 has not yet been pierced, the increased resistance thus indicates that a test strip is still present. It is of course obvious that a check can also be carried out in other ways, for example optically. The counter is then reset and the test strips are successively presented in order by a stepwise advancement.

However, if there is no test strip at the first position N1, the stored position Nx of the test strip presented last before the device actuation, e.g. the opening and closing of the device, is moved to. This can be simply accomplished by a certain drum rotation corresponding to the difference in position. It is also possible that the rotation path after the device actuation until reaching the first position is registered and that the drum is positioned back by a certain distance when the first test strip is not present.

When the last known chamber (Nx) is reached, the presence of a test strip 16 is again checked. If the test strip is present, the following chambers 30 are approached firstly for subsequent tests until the maximum number Nmax is reached. It is, however, also conceivable that the user has inserted a second partially used test strip drum of the same batch so that no test strip may be present at the position Nx. In this case the following positions Nx to Nmax are moved to in steps until possibly a test strip is found.

The process described above is not limited to the insertion of test strip drums. Other replaceable magazines such as disk or stack magazines or tape cassettes and other analytical test elements for example test tape fields or chips basically also come into consideration. An application is also conceivable in the case of any (integrated) disposables, such as test elements which fulfill a lancing and/or detection function in the analysis of body fluids.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A method for operating an analytical system comprising:
   inserting a disposable unit comprising a plurality of test elements in a given order including a first in order position of the disposable unit into a device, the device comprising a device drive coupleable with the disposable unit;
   operating the device drive to present the test elements successively at a measuring position;
   after a predetermined device actuation, activating the drive to position the disposable unit such that the first in order position is at the measuring position, wherein no usable test element is present at the first in order position;
   determining whether a usable test element is present in the disposable unit at the first in order position; and
   upon a determination that no usable test element is present at the first in order position, activating the device drive to position at the measuring position a last presented position of the disposable unit presented before the predetermined device actuation.

2. The method according to claim 1, further comprising storing in a memory of the device an identifier (N) for the last presented position of the disposable unit, wherein the step of positioning the last presented position of the disposable unit is performed according to the identifier (N).

3. The method according to claim 1, further comprising recording the required travel path to position the first in order test element after the predetermined device actuation, wherein the step of positioning the last presented position of the disposable unit is performed according to the travel path.

4. The method according to claim 1, further comprising determining whether a usable test element is present in the disposable unit at the last presented position, and upon a determination that no usable test element is present at the last presented position, executing a sequence of steps determined by the order of the test elements in the disposable unit until a usable test element is presented.

5. The method according to claim 1, further comprising indicating the test readiness of the device when a presented test element is determined to be usable.

6. The method according to claim 1, wherein the predetermined device actuation comprises one or more actuations selected from the group consisting of an operation by a user associated with a possible replacement of the disposable unit, insertion of a disposable unit, the locking of a device component, and the closing of a device cover.

7. The method according to claim 1, wherein the test elements are arranged as test strips each in one allocated cavity, and wherein determining the presence of a usable test element comprises checking the presence of a test element in the respective cavity.

8. The method according to claim 1, wherein the disposable unit comprises a rotatable magazine having the form of a drum magazine or a disk magazine, the magazine comprising a plurality of segments, and wherein the given order of test units is determined by the angular position of the segments.

9. The method according to claim 1, wherein the disposable unit comprises a code that can be scanned by the device, and wherein the code is read between the predetermined device actuation and the positioning of the first test element.

10. The method according to claim 9, wherein the code comprises a barcode, the method further comprising scanning the barcode without contact while the disposable unit is rotated within the device.

11. The method according to claim 1, further comprising counting by a counter of the device when the test elements are used for a measurement, and storing the counted number of used test elements in the counter until the disposable unit is replaced.

12. The method according to claim 1, wherein the test elements are test strips.

* * * * *